United States Patent
Lewis et al.

[11] Patent Number: 6,054,696
[45] Date of Patent: Apr. 25, 2000

[54] FEEDBACK SYSTEM TO AUTOMATICALLY COUPLE MICROWAVE ENERGY INTO AN APPLICATOR

[75] Inventors: David Andrew Lewis, Carmel; Stanley Joseph Whitehair, Peekskill, both of N.Y.

[73] Assignee: International Business Machines Corporation, Armonk, N.Y.

[21] Appl. No.: 09/002,719

[22] Filed: Jan. 5, 1998

Related U.S. Application Data

[60] Provisional application No. 60/034,717, Jan. 6, 1997.

[51] Int. Cl.[7] ............................................. H05B 6/70
[52] U.S. Cl. ..................... 219/690; 219/691; 219/694; 219/696; 219/715; 219/750
[58] Field of Search .................... 219/690–701, 219/702, 715, 745, 746, 750, 752, 753

[56] References Cited

U.S. PATENT DOCUMENTS

| | | |
|---|---|---|
| 3,461,261 | 8/1969 | Lewis et al. ............................. 219/696 |
| 3,784,777 | 1/1974 | Soulier ................................... 219/690 |
| 4,771,153 | 9/1988 | Fukushima et al. .................... 219/690 |
| 5,471,037 | 11/1995 | Goethel et al. ......................... 219/750 |

*Primary Examiner*—Tu Ba Hoang
*Attorney, Agent, or Firm*—Thomas A. Beck

[57] ABSTRACT

A microwave processing system comprising a microwave applicator and a microwave source. A microwave source generates a microwave field at an output frequency. A frequency of the microwave field in the elongated chamber and the output frequency of the microwave source are matched through the use of controlled feedback of critical material and process parameters.

15 Claims, 2 Drawing Sheets

FEEDBACK SYSTEM TO AUTOMATICALLY COUPLE MICROWAVE ENERGY INTO AN APPLICATOR

This application claims the priority from U.S. Provisional Application No. 60/034,717 filed Jan. 6, 1997.

FIELD OF THE INVENTION

The present invention relates to microwave applicators and, more particularly, to a system for matching an input frequency with the resonant frequency of a loaded applicator.

BACKGROUND OF THE INVENTION

Microwave radiation can be applied to a material in a number of ways, using single mode, multimode applicators, traveling wave applicators, slow wave applicators, fringing field applicators and through free space. Each of the aforementioned methods of coupling microwave energy into a material has its advantages and disadvantages which usually depend on the dielectric properties, size and shape, of the materials to be heated and the type of processing (batch, continuous, . . . etc.) to be performed.

Efficient microwave energy transfer is a function of many variables as processing occurs. A number of these variables are material related, e.g., the material type and density and material temperature as well as the time history of both the material temperature and the applied electric field. As the material is heated, the dielectric constant may exhibit hysteresis in temperature and electric field strength. Depending on the nature of the change of the dielectric constant, this may result in the application of a non-uniform electric field or thermal runaway, e.g., hot and cold spots within the material or a mismatch between the resonant frequency of the loaded applicator and the microwave energy source. As the dielectric properties of the load change, the properties of the loaded applicator also change, for example, the resonant frequency of the applicator may change.

Other factors that influence coupling are related to the applicator, material geometry and size and the frequency or wavelength of the electromagnetic energy. Electromagnetic coupling depends on applicator size and geometry, material size and shape, the position of the material within the applicator, and even the relative sizes and shapes of the material and the applicator. In addition, both the applicator and material dimensions may change during heating which further complicates the efficient transfer of energy to the material.

Accordingly, a problem arises when attempting to maintain efficient coupling of the microwave energy into the applicator. This is especially difficult with a single mode, high Q factor applicator. This type of applicator can be tuned to specific electric field patterns (resonance modes) by varying the volume of the applicator. This, however, is laborious and provides difficult process control.

One such approach is found in U.S. Pat. Nos. 4,507,588, 4,585,668, 4,630,566, 4,727,293, and 4,792,772 (Asmussen), all of which disclose methods and apparatuses in which a single mode resonant microwave applicator can be critically coupled by varying two separate, almost orthogonal variables, specifically the cavity length (by moving a short circuit) and the antenna position.

The Asmussen devices include a variable penetration antenna structure which acts to launch radiation into the applicator. The main advantage of the Asmussen device is that it enables complete critical coupling over a wide range of impedance's (generated by the load in the applicator) and without the use of any external coupling structure. Critical coupling can thus be achieved by moving the short and the antenna appropriately.

By moving the flat part of the cavity wall (in a cylinder) in the z-direction (e.g., along the centerline of the cylinder), a wide range of electromagnetic modes can be established and maintained, even as the load varies (due to processing, e.g., temperature changing, material curing, etc.) As a result, if the load changes during processing (e.g., the dielectric properties change, due to increased temperature, curing, phase change in the material and so forth), the resonant frequency in the cavity changes from an initial, fixed processing frequency, usually 2450 MHz or 915 MHz (which are the ISM bands allowed by the Federal Communication Commission (FCC)). It should be understood that the output frequency of a magnetron, by far the most common microwave generating device available, is relatively narrow and is a fixed frequency (because the device itself is a resonant device) and cannot be conveniently varied over a wide range of frequencies dynamically.

U.S. Pat. No. 5,471,037 (Goethal) discloses a single mode cylindrical applicator that operates in the $TM_{02n}$ resonant mode. The microwave applicator is designed to process monomers in order to produce prepolymers. The size of the microwave applicator is selected according to the particular monomers being processed (e.g., fixed dimension applicator). Therefore, there is no mechanism for altering the diameter of the applicator to account for substantially different loads or substantially different dielectric properties.

U.S. Pat. No. 3,461,261 (Lewis) relates to a $TM_{02n}$ applicator that processes threads and yarns with the workpieces passing along the central axis of the applicator. The dimensions of the microwave applicator are selected according to the materials being processed (e.g., fixed dimension applicator).

The electric field pattern sustained by the $TM_{0y0}$ series of modes, where y=1, 2 or greater, is oriented along the z-axis of the applicator and is of constant intensity along the entire length of the applicator for an empty cavity. This is an ideal mode for the processing of wide web-like materials. Referring to FIG. 1 (a mode chart), it can be seen that the $TM_{010}$ mode is independent of the cavity length. Therefore, a low loss, infinitely long applicator is capable of sustaining the same electric field intensity throughout the length.

In all of the aforementioned prior art, all of the available methods rely upon a mechanical change of dimension of the applicator to match the resonant frequency of the applicator with the output frequency of the microwave source. This can be accomplished through the use of stepper motors and sometimes complex, computer driven feedback loops and are slow because of the time required for a motor to complete motion before another iterative measurement of the degree of tune is taken and the tune further improved.

Accordingly, an object of the present invention is to provide a means to maintain maximum coupling efficiency of microwave energy to a microwave applicator through the use of controlled feedback of critical material and process parameters.

It is a further object of the invention to provide a microwave applicator whereby field interactions with the material being processed are controlled through matching of the output frequency of the microwave source to the loaded applicator.

Another object of the invention is to provide a means for only allowing the desired mode and therefore electric field pattern within a loaded microwave applicator automatically through the use of a controlled feedback of critical material and process parameters.

SUMMARY OF THE INVENTION

A means to automatically maintain maximum coupling efficiency of a microwave source to a loaded microwave applicator automatically by controlled feedback. The loaded microwave applicator itself acts as a filter to provide a signal to the microwave source, forcing the source to match the resonant frequency of the loaded applicator. A frequency of a microwave source and loaded microwave applicator are thereby matched through the use of controlled feedback of critical material and process parameters.

DETAILED DESCRIPTION OF THE INVENTION

Figure 1:
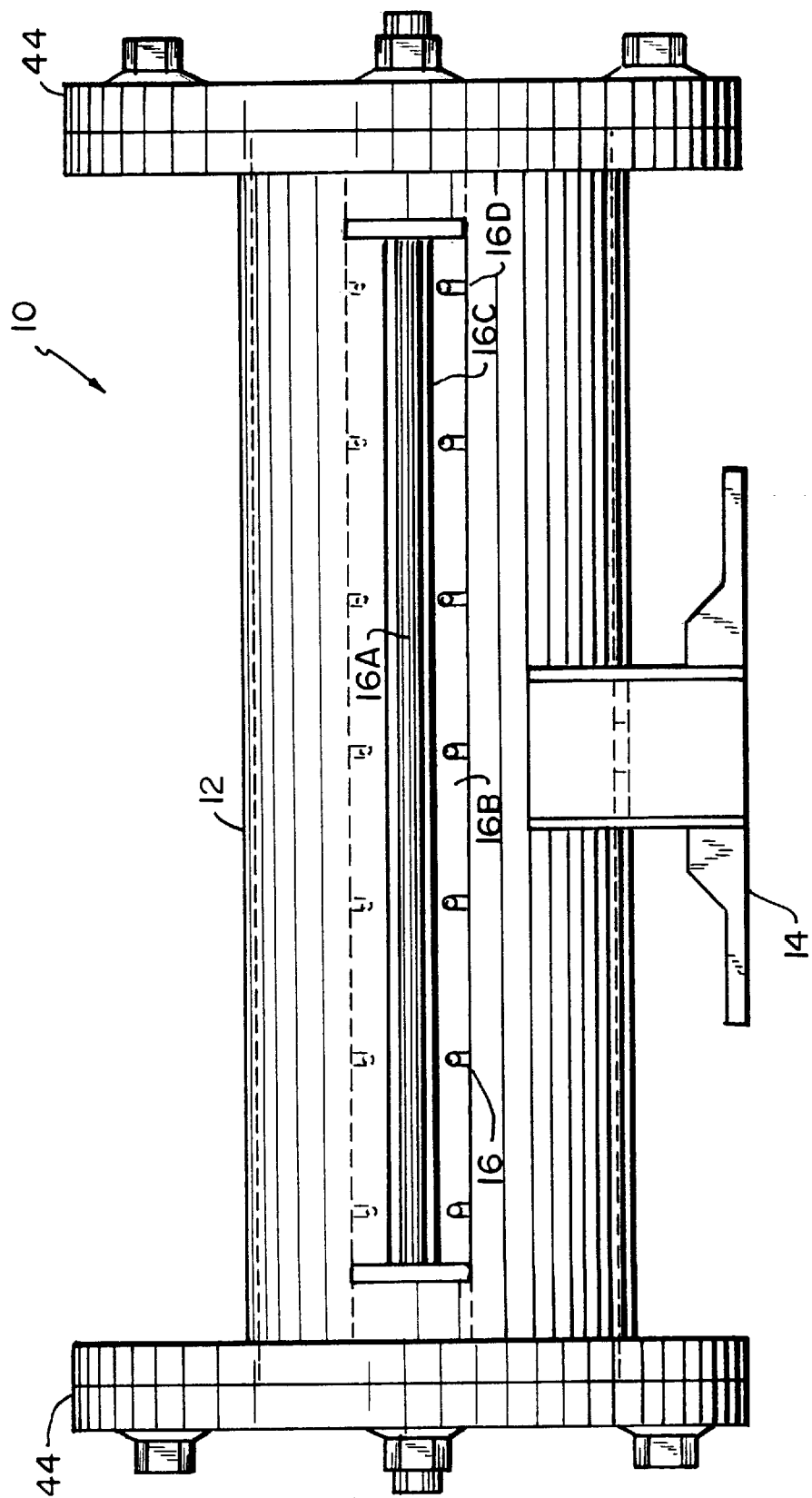
FIG. 1 illustrates a microwave applicator in accordance with the present invention.

Referring to FIG. 1, a microwave applicator 10 in accordance with the present invention includes an elongated chamber 12 with a means for coupling microwave energy, either through a side launch as shown or an end launch structure and a means for introducing a workpiece to be processed. FIG. 1 shows a schematic specifically designed to process a continuous, wide sheet-like material using the TM010 mode (a length independent mode, ie without a node across the width of the applicator). Conventionally, the applicator would have a means for varying the length, through a movable short, or the width by varying the diameter of the applicator, as shown in co-pending application U.S. Provisional Application No. 60/034,717 filed Jan. 6, 1997.

A waveguide 14, coupled to elongated cylinder chamber 12, propagates a microwave field into elongated chamber 12. The waveguide 14 can be connected to a waveguide to coaxial adapter, which allows a coaxial cable to transmit the microwave power from the microwave source to the applicator.

In order to control and maintain microwave field uniformity during material processing and to overcome the difficulty in changing effective cavity dimensions, the present invention provides a novel configuration for tuning the resonant frequency of microwave applicator 10 through the use of controlled feedback of critical material and process parameters. The various preferred embodiments will be discussed in detail below.

Figure 2:
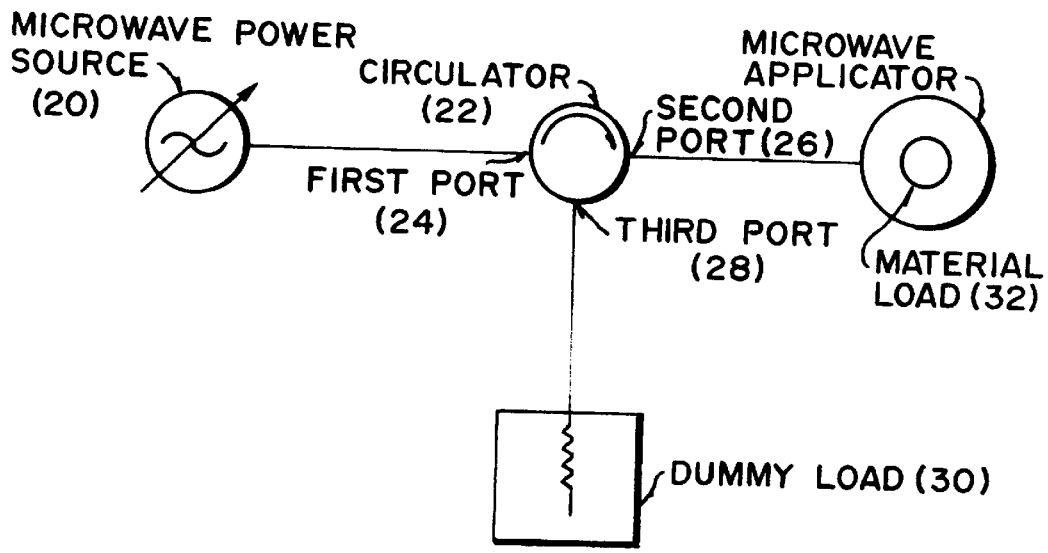
FIG. 2 illustrates a conventional block diagram for a high power microwave circuit.

Referring to FIG. 2, it is normally desirable to provide minimal reverse coupling of the microwave applicator 10 to the power source 20 since excess reflected microwave energy results in unstable operation of the power source and can result in overheating of the source 20 and hence reduced lifetime. Hence a circulator 22 with 3 ports (24, 26 and 28) and dummy load 30 is conventionally used. Microwave energy passes freely from port 1 (24) to port 2 (26) in the forward direction and freely from port 2 (26) to port 3 (28) in the reverse direction, resulting in the reflected microwave power being transferred and dissipated in the dummy load 30. Only a poor impedance match between the dummy load and 28 will result in any radiation being transferred to port 1 (24) from port 3 (28).

Figure 3:
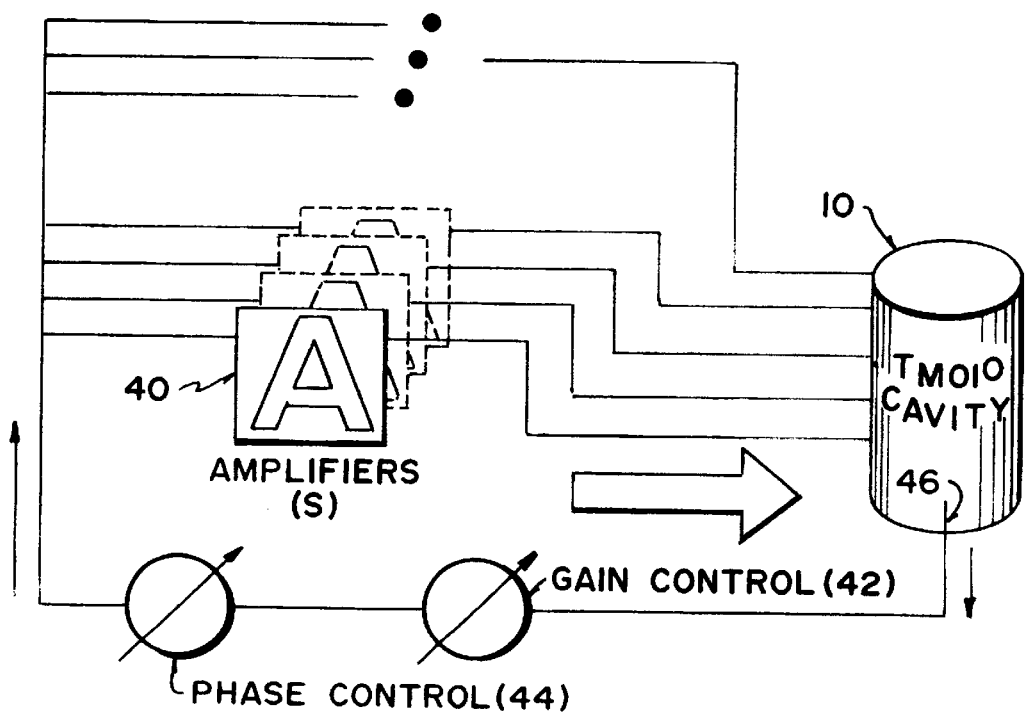
FIG. 3 illustrates a block diagram of a first embodiment of the microwave applicator in accordance with the present invention.

Referring to FIG. 3, a first embodiment of the present invention includes a microwave source 20 preferably having a broad bandwidth which is automatically tuned to the frequency of microwave applicator 10 through the use of controlled feedback of critical material and process parameters from the applicator. In particular, critical material and process parameters are fed back to microwave source 20 by utilizing the applicator as a band-pass filter and sampling the radiation from within the applicator and directing the radiation towards the broadband source 20. This has the effect of using the resonance of the applicator as the source of radiation to the broadband source 20, which will then match the output frequency of the broadband source to the resonance of microwave applicator 10.

In the event that the resonant frequency of microwave applicator 10 moves (due to a change in the dielectric properties of the load due to changing chemistry, temperature, change in composition, etc), the frequency of the radiation being sampled within the microwave applicator 10 will therefore change and hence the amplified signal from the microwave source 20 will change to match the properties of the applicator.

In this embodiment, the transmitted radiation is utilized as a frequency lock-in signal for microwave source 20. This method is very fast, with a time scale of microseconds, but relies upon microwave source 20 having sufficient bandwidth and the exclusion of other resonant frequencies in the range onto which microwave source 20 can lock.

There are currently a number of methods for generating high power microwave energy, such as using a magnetron, klystron, gyrotron, traveling wave tube (TWT) and solid state amplification. Of the aforementioned microwave sources, by far the lowest cost method of generating microwave energy is the cavity magnetron (which is found in all home microwave ovens). Although cavity magnetrons are inexpensive, they have a very narrow output spectrum (bandwidth) and can only be pulled or moved about 10 to 15 MHz at 2.45 GHz. Other types of magnetrons, including coaxial types, have a much greater range over which the output frequency can be pulled, but tend to be more expensive and limited in power output. Gyrotrons and klystrons also operate over a very narrow bandwidth. In this embodiment, it is preferred that microwave source 20 is a broadband source, such as a TWT, or a solid state amplifier.

FIG. 3 illustrates a first embodiment of microwave applicator 10 which employs a frequency locking structure to pull the frequency of the microwave source to that of the applicator. To accomplish the foregoing, a plurality of very broad band microwave supplies 40, such as TWT amplifiers or solid state amplifiers, are utilized to match a substantially wider range of resonant frequency loads, ranging from approximately 100 MHz to approximately 300 MHz. It is, however, preferable that microwave supplies 40 have a bandwidth between approximately 5–50% of the output frequency. A probe 46, positioned in elongated chamber 12 of microwave applicator 10, transmits a signal containing critical material and process parameters of elongated chamber 12 back to microwave supplies 40, across a gain control module 42 and phase control module 44. The judicious positioning of probe 46 can result in the elimination of certain modes, since there will be no coupling of the electric field from that point in the elongated chamber back to the amplifier—hence spurious modes occurring at a frequency different to the desired mode can be eliminated.

As can be seen, this is accomplished by feeding some of the microwave radiation (i.e., the signal) in elongated chamber 12 initially to gain control module 42 and phase control module 44, via probe 46. Gain control module 42 monitors the amplitude of the microwave radiation and ensures that the microwave input of the microwave supplies 40 is within a predetermined amplitude range so that there is sufficient signal strength to be amplified, but not too much power which would result in the destruction of the power supply 40. Thereafter, phase control module 44 adjusts or tunes the input phase of microwave supplies 40 to prevent beating of the power supply and resulting in variable input power to the elongated chamber 12. Typically, the phase control is fixed in the initial setup of the feedback loop and does not require adjustment thereafter.

In the preferred embodiment, a broadband solid state amplifier is used to amplify the signal samples from the microwave applicator. Initially, a broadband frequency source or noise is fed into the microwave applicator. The resonant frequency of the loaded applicator is then sampled by a probe inserted into the microwave applicator and the signal from that probe fed to the input stage of the amplifier.

There are a number of challenges to accomplishing this since the electric field strength in the microwave applicator will increase substantially from the initial state in which minimal microwave power is sampled from the applicator to full power operation in which the power fed back may drive the amplifier into saturation or destroy the input stage of the amplifier. However, if the signal being input to the amplifier is too small, signal strength noise may dominate and the feedback effect is negated. The role of the gain control module, 42, is to provide a stable input power level to the amplifier.

To overcome this the potential of saturation of the input signal, a power limiter can be used. Power limiters are typically employed in receivers to protect the front end of these units from excess power. There are several kinds of limiter, however, the most common kind uses diodes to limit the signal. Diode limiters have good high power protection capabilities but can, but can have distortion problems. Diode limiters can not provide input boost for low power signals going into the amplifier.

A unity gain amplifier is simply an amplifier that is designed to produce the same amount of output power regardless of the input signal strength. The disadvantage of these devices is that they are sensitive to power surges and can be destroyed easily. However, due to the relatively low cost of these devices compared to the high power amplifiers used in the next stage, it is more desirable that the unity gain device be destroyed accidentally than the power amplifier.

A variable attenuator provides a similar function as the diode limiter and provides less distortion, but is more complex. In this type of device, the input signal is attenuated by an amount that increases with power coming into the attenuator, thus providing a constant output power.

For the first, second and third embodiments, microwave radiation can be coupled into microwave applicator 10 using an iris, loop or antenna placed on the outer surface of elongated chamber 12 or from the end of elongated chamber 12 (e.g., end launch). The choice between the aforementioned devices depends on the material to be processed, the manner in which the dielectric properties change during processing and the resonant mode being utilized. Multiple launchers can also be used to improve uniformity and to generate higher power levels in the cavity. They allow the resonant cavity of microwave applicator 10 to act as a power combiner and, at the same time, can be used to minimize any non-uniformities.

In summary, the present invention provides a system in which the output from a microwave applicator automatically tunes the output frequency of the microwave source to that of the applicator for varying loads by utilizing controlled feedback of critical material and process parameters. As can be appreciated, the resonant frequency in the microwave applicator can be maintained without varying the structural dimensions of the applicator.

The invention having thus been described with particular reference to the preferred forms thereof, it will be obvious that various changes and modifications may be made therein without departing from the spirit and scope of the invention as defined in the appended claims.

It is usual that a particular electric field pattern is desired for a particular load. For example, for a flat surface to be processed, a $TE_{111}$ mode is desirable, for a tubular structure, a $TM_{02x}$ mode is more desirable and for a wide web of material, a $TM_{010}$ length independent mode is desirable. Each of these modes can be excited in a particular microwave applicator by providing the correct launch structure. If the applicator is cylindrical in shape, the $TE_{111}$ mode can be excited by a straight antenna or a loop antenna mounted in the side of the cylinder at a maximum field region, while a waveguide launch placed in the same position would not be able to excite that mode. Similarly, by placing the antenna at a null point in the electric field of the mode would result in the mode not being able to be excited. Hence, the judicious placement of a launch structure, certain modes can be prevented from being launched and sustained in the applicator. This knowledge can be used to prevent the excitation of certain unwanted modes.

However, modes such as the $TE_{111}$ mode have a number of higher order analogous modes, $TE_{112}$, $TE_{113}$ for example, in which the electric field pattern repeats in the z-direction. These modes occur at higher frequencies than the base mode. Unfortunately, even through good design and placement of a launch structure, more than one mode can be simultaneously excited if the bandwidth of the power amplifier was great enough. With the use of conventional magnetron power supplies this is less problematic due to the very narrow bandwidth of those devices. In the case where a very wide bandwidth power amplifier were to be utilized with a feedback system as is the object of this invention, it is important to be able to exclude power from going to these modes and therefore maintain a pure electric field pattern within the applicator and therefore in the material being processed.

In the present invention, a signal is being sampled from the microwave applicator to be used as the input to the power amplifier. With the case of a broadband power amplifier supplying an applicator in which a number of modes exist simultaneously, a number of different frequencies will be fed back to the power amplifier. The power amplifier will then amplify all of these frequencies by the same amount with the relative output power of each frequency directly dependent on the power level on the input side of the amplifier and gain of the power amplifier for each frequency (since most amplifiers are not completely linear with frequency), thereby providing a frequency which will be fed back to the amplifier, and so on.

Since it is not desirable to have these unwanted modes, it is important to exclude portions of the output spectrum of the power amplifier from being fed back to the amplifier. This can be accomplished in a number of ways: (i) judicious placement and design of sampling antennas; (ii) bandpass filters between the sample port and the power amplifier; (iii) electronic, dynamic control over output spectrum of the power amplifier (specifically to limit the frequency range of the power amplifier).

In a similar fashion to being able to prevent the launch of certain modes by the placement and type of the launch structure, it is also possible to limit the modes being sampled in the applicator. For example, if a probe antenna was inserted into the side of a cylindrical applicator and a single TM mode was present, the antenna would not be able to pick up the field and hence it would appear that no mode was present. If a loop antenna was placed in the same position, a field would be able to be detected. Similarly, if the loop antenna was placed at a position corresponding to a null in the field, no mode would be detected because there is no coupling to the probe. Therefore, by the judicious design and placement of a coupling probe, the types of modes that can be sampled can be limited. By limiting the number of possible resonant frequencies being sampled by the sampling probe, the number of spurious modes being feedback to the amplifier can also be restricted. It is important to note that through the wrong design of placement of the sampling probe, the desired mode may not be obtained either.

By using more than one probe, two or more signals can be sampled simultaneously and fed to the amplifier. In this case, a gain control amplifier would be used after each probe to ensure the correct level of signal is set before recombination of input signals before the amplifier for amplification into the microwave applicator. Such an arrangement may provide more uniform processing over large sample sizes.

Bandpass filters are relatively straightforward devices that are well known in the electronics industry. Normally, they are designed for relatively low power levels and are relatively inexpensive. A bandpass filter could be used either before the power amplifier (and therefore restrict the range of frequencies (preferably one) being allowed to go to the amplifier) or after the amplifier and limit the frequencies (preferably to one) going to the applicator. There are several disadvantages of the second approach (i.e. placing the bandpass filter after the power amplifier): (i) The amplifier would not be as efficiently amplifying the frequency desired; (ii) the filter would have to be able to cool the energy being dissipated at the unwanted frequencies; (iii) a high power capability is expensive. By placing the device before the power amplifier, only the desired frequency (or frequencies) are allowed to be transmitted to the amplifier.

In the case where it is desired to launch two or more different frequencies in to the microwave applicator simultaneously, the signal from the applicator is split (if one probe can sample two modes) and a bandpass filter adjusted to each of the desired frequencies is placed before the amplifier on each of the split cables. The signals are then combined from each of the split cables at the amplifier. The gain is individually adjusted to provide the desired level of power at each mode.

All of the previous examples site direct feed back techniques. Indirect feedback techniques are also possible. In this technique a signal other than primary driving signal is used.

One example of this is to feed back the output signal from the cavity to a discriminator. The discriminator is a circuit device that converts frequency into voltage and is commonly used in communication devices. This voltage is then used to drive a voltage controlled oscillator (VCO). The VCO's output can then be used to drive the power amplifier driving the cavity. The VCO has the advantage that it provides constant power output and a single frequency with no harmonics. Further, the frequency range can be limited by controlling the voltage between the discriminator and the VCO.

Another example of a indirect feedback is to use a higher harmonic of the resonant cavity as the feedback signal. The principle advantage of this is that these harmonics have much less power than the signal at the primary driving signal making the higher order harmonics easier to filter and control. For example if the 2nd harmonic of the $TM_{010}$ mode is used (the resonant $TM_{020}$ mode) the signal can then be feed through a 2x divider (a common communication circuit) and feed into the driving amplifier.

Another example of a indirect feedback is to mix the frequency down in frequency, filter and condition it, then mix it back up to drive the power amplifier. Typically in communication circuits this is called hedrodyning and the circuitry for doing it is common and well understood. For example, the output of the cavity would be feed into a circuit called a mixer with another signal typically an I.F. (intermediate frequency). The mixer produces the multiplication of the 2 signals. If the IF frequency is carefully selected part of this product is much lower in frequency (exactly dependent and controlled by the IF frequency) and can be separated for the other components by bandpass filtering. This lower frequency signal can then filtered and conditioned using conventional rf technology including devices such as programmable signal conditioners that are now available. The signal could also be digitized and processed in a computer. Finally the conditioned and filtered signal is mixed back up to the desired range of the power amplifier and used to control the cavity.

What is claimed is:

1. A microwave system for automatically providing substantially complete coupling of microwave energy to a microwave applicator comprising:
   a chamber containing a material load to be heated with microwave energy with a characteristic resonant frequency;
   a source to generate microwave energy suitable for being supplied to said chamber;
   means for sampling said microwave energy from said chamber;
   means for transmitting said sampled microwave energy to a microwave amplifier device;
   means for transmitting amplified energy to said chamber.

2. A microwave system as defined in claim 1, wherein said sampling means is designed and placed to sample only microwave energy from a predetermined electromagnetic mode present in said chamber, thereby sampling only the frequency of the mode at the exclusion of all other frequencies.

3. A microwave system as recited in claim 1 where the chamber sustains multiple electromagnetic modes simultaneously.

4. A microwave system as recited in claim 1 where chamber sustains a single electromagnetic mode.

5. A microwave system as recited in claim 1 wherein said source to generate microwave energy is selected from the group consisting of a solid state amplifier and tube amplifier.

6. A microwave system as recited in claim 5 in which the tube amplifer is selected from the group consisting of traveling wave tube amplifier, klystron and gyrotron.

7. A microwave system as recited in claim 1 where gain control is used to control said sampled microwave energy to said microwave amplifier device at a variable predetermined level.

8. A microwave system as recited in claim 7 where said gain control is selected from at least one of unity gain amplifier, bandpass filters and diode limiters.

9. A microwave system as cited in claim 7 in which the gain control is comprised of a voltage controlled oscillator driven by a frequency to voltage discriminator.

10. A microwave system as recited in claim 5 wherein said amplifier device emits an output signal ranging between 100 MHz and 300 MHz.

11. A microwave system as defined in claim 1, further comprising probe means, positioned in said chamber, for sampling said material load and transmitting a signal containing material load and process parameters of said chamber to controlling means wherein said controlling means in response to said material load and said process parameters, causes said microwave energy to match said characteristic resonant frequency.

12. A microwave system as recited in claim 1, wherein said microwave amplifier device is directly coupled to said chamber.

13. A microwave system as recited in claim 1, wherein said microwave amplifier device includes amplifier means having a large bandwidth.

14. A microwave system as recited in claim 1, further comprising means for controlling said characteristic resonant frequency of said chamber.

15. A microwave system as recited in claim 1, wherein said characteristic resonant frequency ranges between approximately 100 MHz and approximately 300 GHz.

* * * * *